United States Patent
Urade et al.

(10) Patent No.: US 7,238,718 B2
(45) Date of Patent: Jul. 3, 2007

(54) METHOD FOR TREATING MYOLYTIC DISEASE AND METHOD FOR SCREENING ANTIMYOLYTIC AGENT

(75) Inventors: Yoshihiro Urade, Kyoto (JP); Naomi Eguchi, Suita (JP); Kosuke Aritake, Kawanishi (JP); Yo Sato, Hyogo-ken (JP); Masako Taniike, Itami (JP); Ikuko Mori, Suita (JP); Masashi Miyano, Hyogo-ken (JP)

(73) Assignees: Osaka Bioscience Institute, Osaka-Fu (JP); Riken, Saitama-Ken (JP)

( * ) Notice: Subject to any disclaimer, the term of this patent is extended or adjusted under 35 U.S.C. 154(b) by 0 days.

(21) Appl. No.: 10/919,473

(22) Filed: Aug. 17, 2004

(65) Prior Publication Data
US 2005/0272767 A1    Dec. 8, 2005

(30) Foreign Application Priority Data
Oct. 14, 2003  (JP) .............................. 2003-353917

(51) Int. Cl.
*A61K 31/41*  (2006.01)
*A61K 31/40*  (2006.01)
*A61K 31/185* (2006.01)

(52) U.S. Cl. ................. 514/357; 514/411; 514/578

(58) Field of Classification Search .............. 800/3
See application file for complete search history.

(56) References Cited
U.S. PATENT DOCUMENTS
2005/0227984 A1 * 10/2005 Urade et al. ............... 514/241

OTHER PUBLICATIONS

Cumming et al, Acta Neurophathol Suppl (Berl), 7:305-307, 1981.*
Okinaga et al, Acta Neuropathology, 104:377-384, 2002.*
Eguchi et al, Proceedings of the National Academy of Science, 94:14689-14694, 1997.*
Urade et al, Prostaglandins and Other Lipid Mediators, 68-69:375-382, 2002.*
Sato et al., "Prevention of Muscular Necrosis By inhibition of hematopoietic prostaglandin D synthase" Program and Abstracts of the 76th Annual Meeting of the Japanese Biochemical Society, Japan 75:(8), 4P-074, Aug. 25, 2003.
Yo Sato et al., "Prevention of muscular necrosis by inhibition of hematopoietic prostaglandin D synthase", (2004), Neuroscience Research, vol. 50, abstract only.

* cited by examiner

*Primary Examiner*—Raymond J. Henley, III
(74) *Attorney, Agent, or Firm*—Browdy and Neimark, PLLC

(57) ABSTRACT

An object of the present invention is to provide a method which is able to prevent or improve the progress of myolytic diseases such as muscular dystrophy. Such an object is able to be solved by a method where an effective dose of an inhibitor for hematopoietic prostaglandin D synthase (H-PGDS) or an antagonist to prostaglandin D receptor is administered to a patient who needs it. The present invention also provides a method for screening compounds which are able to prevent the progress of myolytic diseases and to improve it using human H-PGDS overexpressed transgenic mice.

6 Claims, 4 Drawing Sheets

METHOD FOR TREATING MYOLYTIC DISEASE AND METHOD FOR SCREENING ANTIMYOLYTIC AGENT

FIELD OF THE INVENTION

This invention relates to a method for the treatment of myolytic disease and to a method for screening of antimyolytic agents. More particularly, it relates to a method for prevention of progress or improvement of myolytic diseases such as muscular dystrophy and to a method for screening of antimyolytic agents. Still more particularly, this invention relates to a method for prevention of exacerbation of myolysis in which prostaglandin $D_2$ is participated and for improving the prognosis by means of inhibition of hematopoietic prostaglandin D synthase (hereinafter, it may be referred to as "H-PGDS") which is induced in mast cells, accumulated macrophages and muscle fibers of myolytic site by diseases such as muscular dystrophy, polymyositis, muscle strain, cardiomyopathy (myocardial infarction) and diabetic angiopathy (vascular smoothth muscle disorder) or by means of inhibition of activation of prostaglandin D receptor (hereinafter, it may be referred to "DP receptor") which is expressed in accumulated Th2 cells or adipocytes or blood vessels near the degenerated site. The present invention further relates to a method for the screening of treating agents for myolytic diseases using human H-PGDS overexpressing transgenic mice.

BACKGROUND OF THE INVENTION

A typical example of myolytic disease is muscular dystrophy. Muscular dystrophy is a general name for refractory muscular diseases where muscle suffers from necrosis and degeneration in a progressive manner whereupon muscle weakness is progressing. Among them, Duchenne's's muscular dystrophy (DMD) is a dystrophy having the highest frequency. In DMD, dystrophin is hardly produced, due to genetic abnormality of dystrophin. Since dystrophin constructs the skeleton of muscle cells, muscular cells in DMD are unable to keep their shape and necrosis easily happens. Cardiac and respiratory disorder caused by muscle weakness results in death.

With regard to a therapy for this disease, gene and transplantation therapies have been attempted but a basic remedy for the disease has not yet been developed. With regard to a drug therapy, a steroid pulse therapy with adrenocortical hormone (refer to Burrow K L, et al., *Neurology*, 41(5):661–6) and administration of antibiotics (gentamicin) (Barton Davis ER, et al., *J. Clin. Invest.*, 104(4): 367–368) have been applied. However, these symptomatic therapies are associated with severe side effects. Furthermore, the therapeutic effect lowers during long-term administration. Especially in the case of DMD, a life-prolongation is expected only for about one year. Expression of H-PGDS increases in necrotic muscles of patients with DMD or multiple myolysis (Okinaga T, et al., *Acta Neuropathol.* (Berl). 2002 October; 104(4):377–84. Epub 2002 June). Therefore, it is likely that substances which regulate expression of H-PGDS and production and/or signal transduction of prostaglandin $D_2$ are able to be effective therapeutic agents for such morbid states.

DISCLOSURE OF THE INVENTION

An object of the present invention is to provide a method which is able to prevent or improve the progress of myolytic diseases such as muscular dystrophy.

Another object of the present invention is to provide a method for screening the compounds which treat myolytic diseases.

In order to achieve the above-mentioned objects, the present inventor has carried out intensive studies and achieved the present invention on the basis of the following findings.

1) For experimental muscular necrosis models, expression of H-PGDS and DP receptors increases in the necrotic muscle fibers;

2) Expression of H-PGDS is induced in mast cells, accumulated macrophage and muscular fiber around the necrotic legion;

3) Macrophages are significantly accumulated around the necrotic legion;

4) Necrotic legion becomes small after administration of an inhibitor for H-PGDS;

5) Necrotic legion becomes small after administration of an antagonist to DP receptor; and 6) Necrotic legion expands in human H-PGDS overexpressing transgenic mice.

Thus, the present invention relates to a treatment for myolytic diseases used for prevention of exacerbation of necrosis and for improvement of prognosis by administration of an H-PGDS inhibitor at an effective dose to a patient with myolytic disorder.

Myolytic diseases include muscular dystrophy, polymyositis, muscle strain cardiomyopathy (myocardial infarction) and diabetic angiopathy (vascular smooth muscle disorder).

Examples of an H-PGDS inhibitor are 4-benzhydryloxy-1-{3-(1H-tetrazol-5-yl)-propyl}piperidine (hereinafter, referred to as "HQL-79"), 1-amino-4-{4-[4-chloro-6-(2-sulfophenylamino)-[1,3,5]triazin-2-ylmethyl]-3-sulfophenylamino}-9,10-dioxo-9,10-dihydroanthracene-2-sulfonic acid (Cibacron Blue), 1-amino-4-(4-sulfamoylaniline)-anthraquinone-2-sulfonic acid (PGD-042), 2-(2'-benzothiazolyl)-5-styryl-3-(4'-phthalhydrazityl)-tetrazolium chloride (PGD-016) and pharmaceutically acceptable salts thereof.

The present invention also relates to a method for treatment of myolytic diseases for prevention and improvement of the progress of refractory muscular diseases such as muscular dystrophy and to a method for administration of an effective dose of antagonist for prostaglandin D receptor to patients who need that.

Examples of the antagonist for prostaglandin D receptor are 3-benzyl-5-(6-carboxyhexyl)-1-(2-cyclohexyl-2-hydroxyethylamino)-hydantoin (BW A868C), (+)-(3R)-3-(4-fluorobenzenesulfonamide)-1,2,3,4-tetrahydrocarbazole-9-propionic acid (ramatroban), (Z)-7-[(1R,2R,3S,5S)-2-(5-hydroxybenzo[b]thiophen-3-ylcarbonylamino)-10-norpinan-3-yl]hept-5-enoic acid (S-5715) and pharmaceutically acceptable salts thereof.

The compound which is used for prevention and improvement of myolytic diseases such as muscular dystrophy used in the present invention comprises H-PGDS inhibitors or prostaglandin D receptor antagonists as mentioned above and they are also able to be screened as follows.

Thus,

1) N-butylpipecolic acid 2,6-dimethylanilide hydrochloride monohydrate (bupivacaine hydrochloride) which is a local anesthetic is intramuscularly injected to human H-PGDS overexpressing transgenic mice, 2) a candidate compound is administered to the transgenic mice before or after induction of myolysis and 3) the state of myolysis in the mice is compared with the state in transgenic mice to which no candidate compound is administered.

A process for the production of human H-PGDS overexpressing transgenic mice is described in the international application PCT/JP00/06963 (WO 01/24627) filed on Oct. 5, 2000, the disclosure of which are incorporated herein for reference.

In the human H-PGDS overexpressing transgenic mice in which H-PGDS is expressed in large quantities, myolysis is much more exacerbated and, therefore, effect of the candidate compound is able to be apparently judged.

EXAMPLES

Example 1

Figure 1:
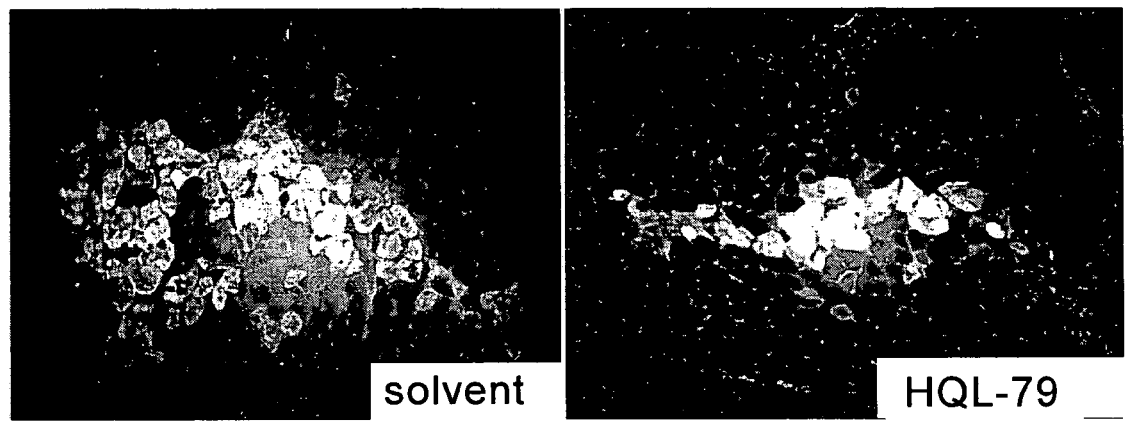
FIG. 1 shows reduction in myolysis induced by bupivacaine hydrochloride and in degenerated region by HQL-79 which is an H-PGDS inhibitor.

Reduction in Myolysis Induced by Bupivacaine Hydrochloride and in Degenerated Region by an H-PGDS Inhibitor Effect of an H-PGDS inhibitor to myolysis was tested using a myolysis model induced by bupivacaine hydrochloride which is an experimental model for muscular dystrophy (Nonaka I, et al., *Acta Neuropathol.,* 60:167–174, 1983). Bupivacaine hydrochloride (0.5 w/v %, 0.1 ml) was injected into gastrocnemius of C57BL/6 mice (K. K. Oriental Bio Service) (eight weeks old; male) to induce myolysis and, after 24 hours, Evans' Blue dye solution (1.0 w/v %) was intravenously injected from tail vein. After 30 minutes, they were killed by excessive anesthetization and perfused with physiological saline solution, gastrocnemius was excised and quickly frozen. The cryosection was prepared and then accumulated Evans' Blue was observed under a fluorescent microscope. Necrotic legion was enhanced by means of fluorescence. In the mice to which an H-PGDS inhibitor (HQL-79) was orally administered (10 mg/kg), degenerated region by necrosis became small (refer to FIG. 1)

Example 2

Quantification of Myolysis Region

Figure 2:
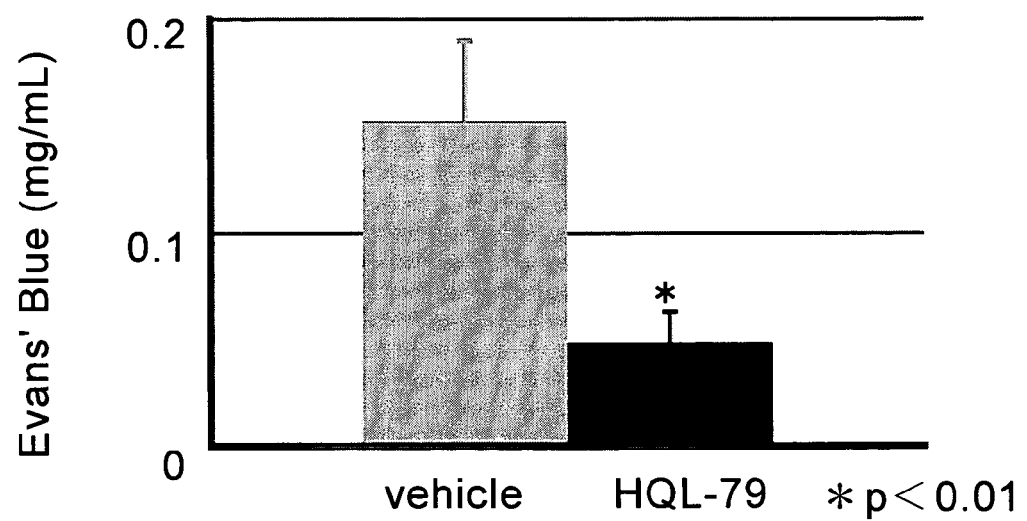
FIG. 2 shows the result of quantification of therapeutic effect of HQL-79 to muscular necrosis by bupivacaine hydrochloride.

Quantification of the degenerated region by necrosis shown in Example 1 was carried out. Evans' Blue was extracted from the freeze-dried gastrocnemius by formamide. After the extraction, absorbance of Evans' Blue (630 nm) was measured calorimetrically. In the group to which HQL-79 was administered, incorporation of Evans' Blue significantly decreased (refer to FIG. 2).

Example 3

Nonoperative Observation of Necrotic Legion Using an X-ray CT

Figure 3:
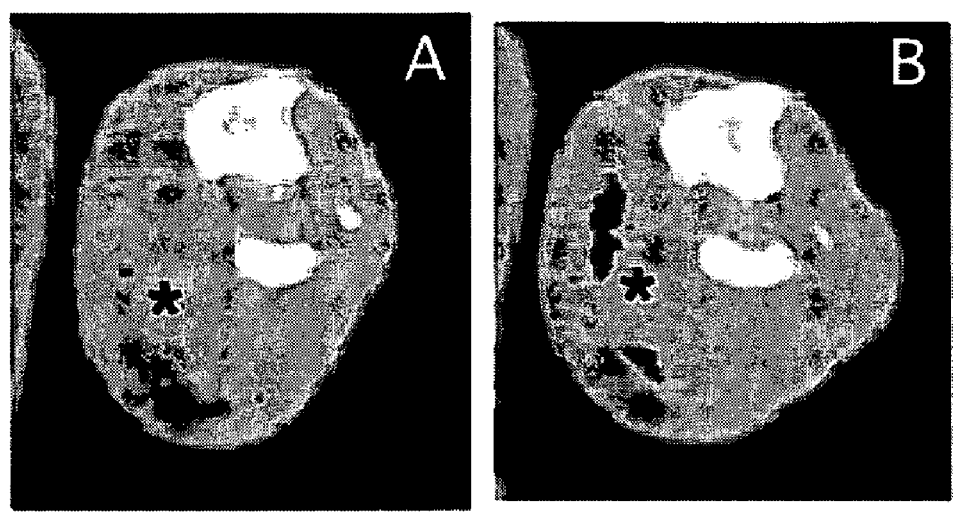
FIG. 3 shows the result of therapeutic effect of HQL-79 to muscular necrosis by bupivacaine hydrochloride, as judged by an X-ray CT. Panel A is the case in which HQL-79 is administered and panel B is the case in which HQL-79 is not administered.

Degenerated region was observed by a nonoperative manner using X-ray CT for experimental animals. N,N'-Bis[2-hydroxy-1-(hydroxymethyl)ethyl]-5-[(2S)-2-hydroxypropanoylamino]-2,4,6-triiodoisophthalamide (iopamidol), an X-ray contrast agent for urinary blood vessels, was intravenously injected from tail vein of mice after one day from the treatment with bupivacaine hydrochloride and a laminogram by an X-ray CT after 15 minutes is shown. A region with specific CT values which is noted in the laminogram of gastrocnemius decreased by administration of HQL-79. In the region where retention of the contrast agent is recognized, bleeding and edema as a result of muscular destruction are noted (refer to FIG. 3).

Example 4

Exacerbation of Myolysis in Human H-PGDS Overexpressing Transgenic Mice

Figure 4:
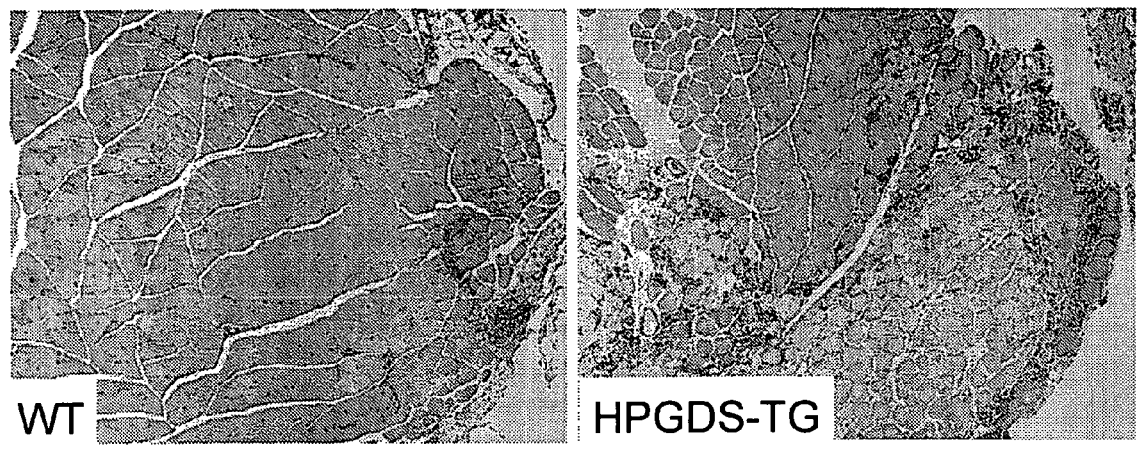
FIG. 4 shows the result of comparison of muscular necrosis induced by bupivacaine hydrochloride between a wild type and human H-PGDS overexpressing transgenic mice.

Muscular necrosis by bupivacaine hydrochloride was compared in mice of a wild type and human H-PGDS overexpressing transgenic mice. After two days from intramuscular injection of bupivacaine hydrochloride, necrotic legion expanded within a broad range in the HPGDS-TG mice than in the wild-type mice (refer to FIG. 4).

Example 5

Figure 5:
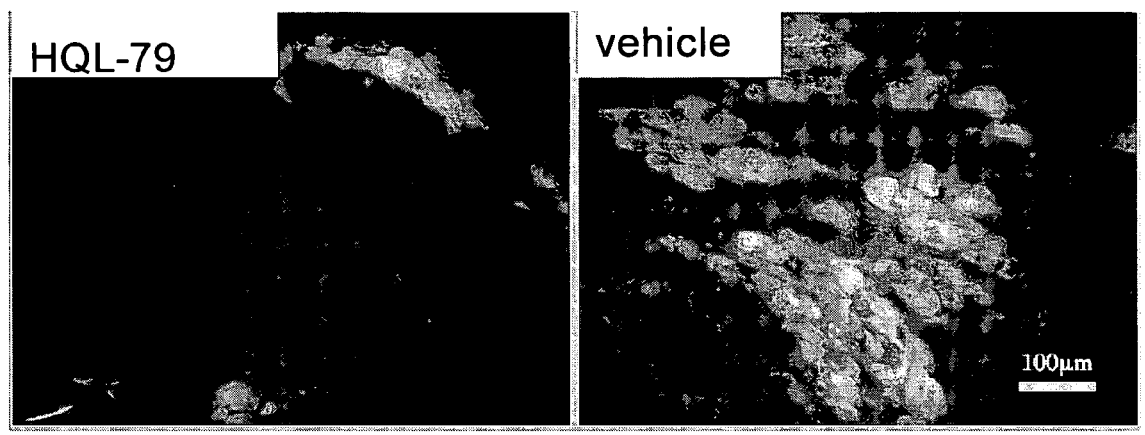
FIG. 5 shows a therapeutic effect of HQL-79 to mdx mice which are model animals for Duchenne's muscular dystrophy.

Therapeutic Effect of HQL-79 in a Model Animal (mdx Mice) for Duchenne's Muscular Dystrophy HQL-79 was continuously administered for two weeks to mdx mice which is a model animal for Duchenne's muscular dystrophy (Bogdanovich S, et al., *Nature,* Nov. 28, 2002, 420(6914):418–21) International Council or Laboratory Animal Science and the effect of the HPGDS inhibitor to myolysis was tested. After two weeks from the initiation of the administration, an Evans' Blue dye solution (1.0 w/v %) was intravenously injected from tail vein. After one hour therefrom, the mice were killed by excessive anaesthetization and perfused with physiological saline solution, the gastrocnemius was excised and quickly frozen. The retention of Evans' Blue in the muscle was observed under a fluorescent microscope. Necrotic lesion was enhanced by means of fluorescence. In the mice to which HQL-79 was administered, retention of the dye (grayish white region) which is an index for myolysis decreased as compared with the group to which a vehicle was administered (refer to FIG. 5).

Example 6

Figure 6:
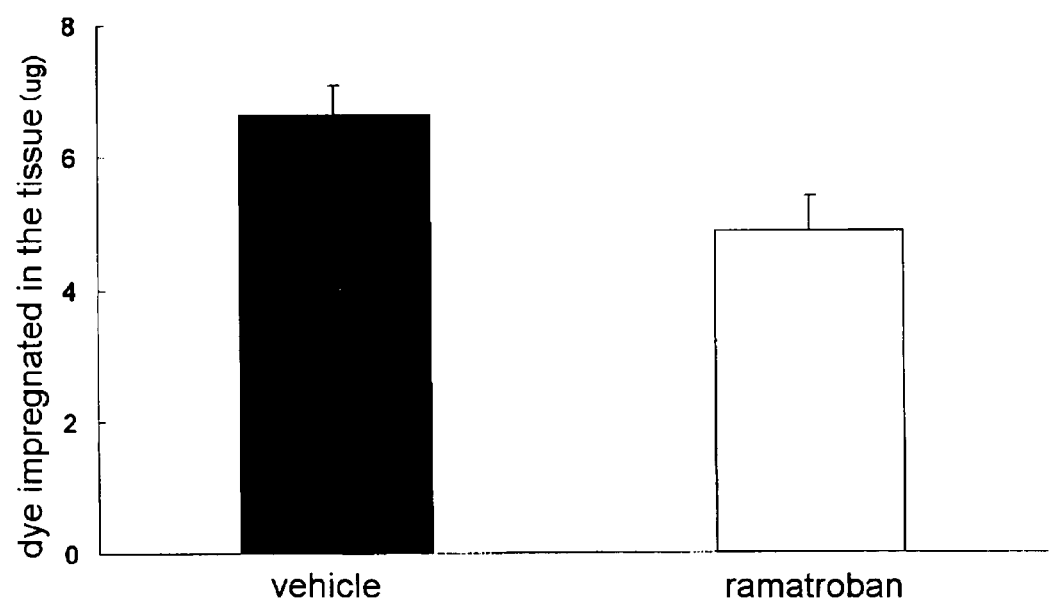
FIG. 6 shows the result of quantification of the therapeutic effect of ramatroban to muscular necrosis induced by bupivacaine hydrochloride.

Effect of Prostaglandin D Receptor Antagonist to a Myolysis Model Induced by Bupivacaine Hydrochloride Effect of prostaglandin D receptor antagonist (ramatroban) to myolysis was tested using a myolysis model induced by bupivacaine hydrochloride. Myolysis was induced by injection of bupivacaine hydrochloride (1 w/v %; 0.05 mL) into gastrocnemius of C57BL/6 mice (8 weeks age; male) to induce myolysis. Ramatroban in a dose of 30 mg/kg was orally administered for two times before one hour and after 18 hours from the intramuscular injection of bupivacaine hydrochloride. After 24 hours from the intramuscular injection of bupivacaine hydrochloride, an Evans' Bluedye solution (1 w/v %) was injected from tail vein. After 1 hour therefrom, the mice were killed by excessive administration of anesthetic agent, the whole body was perfused with physiological saline solution and gastrocnemius was excised. After the excised tissue was freeze-dried, the dye incorporated into the tissue was extracted with formamide and amount of the dye was colorimetrically determined from the absorbance (630 nm). In the group to which ramatroban was administered, the amount of Evans'' Blue impregnated into the tissue lowered (refer to FIG. 6).

Preparation 1

Production of Human Hematopoietic Prostaglandin D Synthase Overexpressing Transgenic Mice The human hematopoietic prostaglandin D synthase overexpressing transgenic mice are produced according to a method disclosed in WO 01/24627.

From a cDNA library prepared from mRNA of human cells, cDNA of human H-PGDS (*Eur. J. Biochem.* 267: 3315–3322, 2000; GenBank Accession No. NM-014485) was cloned using cDNA of rat H-PGDS gene as a probe (*Cell* 90:1085–10975, 1997; GenBank Accession No. D82071). After that, cDNA of human H-PGDS was inserted into and bonded to a cloning site (Sal I/Not I) of a vector pCAGGS (*Gene* 108:193–199 (1991)) and a transferred vector was constructed. The transferred gene has a CMV enhancer and a chicken β-actin promoter at an upstream area of H-PGDS cDNA and, when it is introduced into chromosomes of mice, H-PGDS mRNA is overexpressed by the action of those enhancer and promoter. The transferred vector was injected into fertilized eggs of FVB mice (obtained from the National Institute of Health Animal Genetic Resources) by means of a microinjection method. The fertilized eggs into which the gene was introduced were transplanted to ovary of a temporary parent according to a common method, grown up to individuals and subjected to birth. DNA was extracted from tail of the resulting mice and, using a probe synthesized according to the sequence of the transferred gene, transgenic mice were selected by the Southern blotting method.

When the hematopoietic prostaglandin D synthase (H-PGDS) inhibitor and/or the prostaglandin D receptor antagonist in accordance with the present invention are/is to be used for the treatment, they/it are/is made into preparations as common oral or parenteral preparations. A pharmaceutical composition containing the hematopoietic prostaglandin D synthase (H-PGDS) inhibitor and/or the prostaglandin D receptor antagonist in accordance with the present invention is able to be in a dosage forms for oral and parenteral administrations. Thus, it may be made into an orally administering preparations such as tablets, capsules, granules, powder and syrup or a parenteral preparations such as injection solution or suspension (e.g., that for intravenous injection, intramuscular injection and hypodermic injection), inhalation agent, eye drops, nasal drops, suppository and preparations for percutaneous administration and for percutaneous absorption (e.g., ointment, plaster and poultice). Preferably, it is used as an orally administering preparation or injection medicine.

Those preparations are able to be manufactured using appropriate carrier, excipient, solvent, substrate, etc. which has been known among persons skilled in the art. For example, in the case of tablets, active ingredients and supplementary components are compressed or molded together. With regard to the supplementary components, pharmaceutically acceptable excipient such as binder (e.g., corn starch), filler (e.g., lactose and microcrystalline cellulose), disintegrating agent (e.g., starch and sodium glycolate), lubricant (e.g., magnesium stearate), etc. may be used. Tablets may be appropriately coated. In the case of liquid preparations such as syrup, liquid and suspension, there may be used, for example, suspending agent (such as methylcellulose), emulsifier (such as lecithin), preservative, etc. In the case of preparations for injection, any of the forms of solution, suspension and oily or aqueous emulsion may be used and that may contain a stabilizer for suspension, a dispersing agent, etc. In the case of preparations for percutaneous administration and for percutaneous absorption such as ointment, plaster and poultice, preparations are produced using an aqueous substrate (water, lower alcohol or polyol) or an oily substrate (higher fatty acid ester (isopropyl myristate) or lipophilic alcohol).

Dose of the hematopoietic prostaglandin D synthase (H-PGDS) inhibitor or the prostaglandin D receptor antagonist in accordance with the present invention is 0.01 to 100 mg or, preferably, 1 to 10 mg per kg body weight a day in the case of oral administration although that varies depending upon dosage form, symptom, age, body weight or sex of the patient, medicine which is used together (if any), etc. and is to be finally decided by medical doctors. In the case of parenteral administration, it is 0.01 to 10 mg, preferably 0.1 to 8 mg or, more preferably, 0.1 to 1 mg per kg body weight a day.

Formulation 1

A gelatin hard capsular preparation of the following composition was prepared by a common method.

| Effective ingredient | 10 mg |
| Starch | 50 mg |
| Magnesium stearate | 10 mg |

Formulation 2

A tablet of the following composition was prepared by a common method.

| Effective ingredient | 10 mg |
| Microcrystalline cellulose | 500 mg |
| Silicon dioxide | 10 mg |
| Magnesium silicate | 10 mg |

As fully illustrated hereinabove, there is provided a method for prevention of exacerbation of myolysis in which prostaglandin $D_2$ is participated and for improving the prognosis by means of inhibition of hematopoietic prostaglandin D synthase which is induced to mast cells, accumulated macrophage and muscle fiber of myolytic site by diseases such as muscular dystrophy or by means of inhibition of activation of prostaglandin D receptor which is expressed in accumulated Th2 cells or adipocytes or blood vessels near the degenerated site. There is also provided a method for the screening of a compound which is able to prevent the progress or to improve the myolysis diseases using human hematopoietic prostaglandin D synthase overexpressing transgenic mice.

What is claimed is:

1. A method for treatment of Duchenne's dystrophy (DMD) or polymyositis (PM), comprising administering an effective dose of an inhibitor for hematopoietic prostaglandin D synthase (H-PGDS) to a patient in need thereof.

2. The method according to claim 1, wherein the H-PGDS inhibitor is selected from the group consisting of 4-benzhydryloxy-1-{3-(1H-tetrazol-5-yl)-propyl}piperidine (HQL-79), 1-amino-4-{4-[4-chloro-6-(2-sulfophenylamino)-[1,3,5]triazin-2-ylmethyl]-3-sulfophenylamino}-9,10-dioxo-9,10-dihydroanthracene-2-sulfonic acid (Cibacron Blue), 1-amino-4-(4-sulfamoylaniline)-anthraquinone-2-sulfonic acid (PGD-042), 2-(2'benzothiazolyl)-5-styryl-3-(4'-phthalhydrazityl)tetrazolium chloride (PGD-016) and pharmaceutically acceptable salts thereof.

3. The method according to claim 2, wherein the H-PGDS inhibitor is 4-benzhydryloxy-1-{3-(1H-tetrazol-5-yl)-propyl}piperidine (HQL-79) or a pharmaceutically acceptable salt thereof.

4. A method for treatment of polymyositis (PM) where an effective dose of an antagonist to prostaglandin D receptor is administered to a patient who needs it.

5. The method according to claim 4, wherein the prostaglandin D receptor antagonist is selected from the group consisting of 3-benzyl-5-(6-carboxyhexyl)-1-(2-cyclohexyl-2-hydroxyethylamino)-hydantoin (BW A868C), (+)-(3R)-3-(4-fluorobenzenesulfonamide)-1,2,3,4-tetrahydrocarbazole-9-propionic acid (ramatroban), (Z)-7[(1R,2R,3S,5S)-2-(5-hydroxybenzo[b]thiophene-3-ylcarbonylamino)-10-norpinan-3-yl]hept-5-enoic acid (S-5715) and pharmaceutically acceptable salts thereof.

6. The method according to claim 1, wherein the patient is one suffering from DMD.

* * * * *